United States Patent
Lemmel et al.

(10) Patent No.: US 7,811,828 B2
(45) Date of Patent: Oct. 12, 2010

(54) METHOD FOR IDENTIFYING AND QUANTIFYING OF TUMUOR-ASSOCIATED

(75) Inventors: Claudia Lemmel, Tübingen (DE); Hans-Georg Rammensee, Tübingen-Unterjesigen (DE)

(73) Assignee: Immatics Biotechnologies GmbH, Tubingen (DE)

( * ) Notice: Subject to any disclaimer, the term of this patent is extended or adjusted under 35 U.S.C. 154(b) by 626 days.

(21) Appl. No.: 10/587,876

(22) PCT Filed: Jan. 28, 2005

(86) PCT No.: PCT/EP2005/000873

§ 371 (c)(1),
(2), (4) Date: May 4, 2007

(87) PCT Pub. No.: WO2005/076009

PCT Pub. Date: Aug. 18, 2005

(65) Prior Publication Data

US 2008/0038285 A1 Feb. 14, 2008

(30) Foreign Application Priority Data

Jan. 28, 2004 (DE) .......................... 10 2004 005 273
Mar. 6, 2004 (DE) .......................... 10 2004 011 503

(51) Int. Cl.
- G01N 33/58 (2006.01)
- G01N 33/53 (2006.01)
- G01N 33/533 (2006.01)

(52) U.S. Cl. ..................... 436/501; 435/7.1; 436/64; 436/504; 436/544; 436/545

(58) Field of Classification Search ................ None
See application file for complete search history.

(56) References Cited

U.S. PATENT DOCUMENTS

| | | | |
|---|---|---|---|
| 2005/0239209 A1 | 10/2005 | Krakover | |
| 2008/0207497 A1 | 8/2008 | Ramakrishna | |

FOREIGN PATENT DOCUMENTS

| | | | |
|---|---|---|---|
| WO | 02046416 | A2 | 6/2002 |
| WO | 03025576 | A2 | 3/2003 |
| WO | WO 03/025576 | A | 3/2003 |
| WO | 2007150077 | A2 | 12/2007 |
| WO | 2008070047 | A2 | 6/2008 |
| WO | 2008088583 | A2 | 7/2008 |
| WO | 2009036246 | A2 | 3/2009 |

OTHER PUBLICATIONS

Beardsley et al., "Optimization of Guanidination Procedures for MALDI Mass Mapping," *Anal. Chem.*, Apr. 15, 2002, pp. 1884-1890, vol. 74, No. 8.

Lemmel et al., "Differential quantitative analysis of MHC ligands by mass spectrometry using stable isotope labeling," *Nature Biotechnology*, Apr. 2004, pp. 450-454, vol. 22, No. 4.

Martin et al., "Quantitative Proteomic Analysis of Proteins Released by Neoplastic Prostate Epithelium," *Cancer Research*, Jan. 1, 2004, pp. 347-355, vol. 64, No. 1.

Moritz et al., "Approaches for the quantification of protein concentration ratios," *Proteomics*, Nov. 2003, pp. 2208-2220, vol. 3, No. 11.

Weinschenk et al., "Integrated Functional Genomics Approach for the Design of Patient-individual Antitumor Vaccines," *Cancer Research*, Oct. 15, 2002, pp. 5818-5827, vol. 62, No. 20.

Phillip, R. et al. "Shared Immunoproteome for ovarian cancer diagnostics and immunotherapy: Potential theranostic approach to cancer," J. Proteome Res. 2007;6(7):2509-2517.

Moritz B. et al. "Approaches for the Quantification of Protein Concentration Ratios", Proteomics, vol. 3, No. 11, Nov. 2003, pp. 2208-2220, XP002359083 ISSN: 1615-9853.

Weinshenk T. et al.: "Integrated Functional Genomics Approach for the Design of Patient-Individual Antitumor Vaccines", Cancer Research, American Association for Cancer Research, Baltimore, MD, US, vol. 62, No. 20, Oct. 15, 2002, pp. 5818-5827, XP002266492 ISSN: 0008-5472.

Beardsley R. "Optimization of Guanidination Procedures for MALDI Mass Mapping", Analytical Chemistry, Apr. 15, 2002, vol. 74, No. 8, pp. 1884-1890, XP002359084 ISSN:0003-27000.

Lemmel C. et al. "Differential Quantitative Analysis of MHC Ligands by Mass Spectrometry Using Stable Isotope Labeling", Nature Biotechnology, vol. 22, No. 4, Apr. 2004, pp. 450-454, XP002359085 ISSN: 1087-0156.

*Primary Examiner*—Misook Yu
(74) *Attorney, Agent, or Firm*—Baker, Donelson, Bearman, Caldwell & Berkowitz, PC

(57) ABSTRACT

Described is a method for identifying and quantifying of tumour-associated peptides, wherein first at least two different sources for obtaining the peptide are provided (tumourous and healthy tissue), and, separately of one another, the peptides from the different sources are chemically modified in an identical manner by using at least two different stable isotopes of the same element. Subsequently, the peptides are isolated by a chromatographic method, and the amino acid sequences of the peptides are determined, wherein the determination of the relative amount ratios of peptides having the identical sequence from different samples one to the other occurs by using a stable isotope in the chemical modification. Furthermore, the invention relates to a tumour-associated peptide having an amino acid sequence that is selected from the group consisting of SEQ-ID No. 1 to 36 from the accompanying sequence protocol, wherein the peptide has the ability to bind to a molecule of the human major histocompatibility complex (MHC) class-I. Furthermore, the invention relates to the use of the peptides for producing a medicament and for the treatment of tumourous diseases and/or adenomatous diseases. Furthermore, a pharmaceutical composition is described that comprises at least one of the peptides.

9 Claims, 4 Drawing Sheets

METHOD FOR IDENTIFYING AND QUANTIFYING OF TUMUOR-ASSOCIATED

CROSS-REFERENCE TO A RELATED APPLICATION

This application is a National Stage Application of International Application Number PCT/EP2005/000873, filed Jan. 28, 2005; which claims priority to German Application Nos. 10 2004 005 273.5, filed Jan. 28, 2004 and 10 2004 011 503.6, filed Mar. 6, 2004.

The present invention relates to a method for identifying and quantifying and a method for producing tumour-associated peptides, and the so identified/quantified/produced peptides as well as to uses thereof.

These peptides are employed, for example, in the immunotherapy of tumourous diseases. The recognition of tumour-associated antigens through components of the immune system plays an outstanding role in the elimination of tumour cells by the immune system. This mechanism is based on the requirement that qualitative or quantitative differences between tumour cells and healthy cells exist. In order to generate a response of the immune system that is directed against the tumour, the tumour cells must express antigens, against which an immune response is generated that is sufficient for an elimination of the tumour.

A particularly large role in the elimination of tumours is played by the CD8-expressing cytotoxic T-lymphocytes (in the following CTL). For triggering of such an immune reaction by CTL, foreign proteins/peptides must be presented to the CTL. T-cells do recognise antigens as peptide fragments only if these are presented by MHC-molecules ("major histocompatibility complex") on cellular surfaces. These MHC-molecules are peptide receptors that normally bind peptides within the cell in order to transport them to the cellular surface. This complex of peptide and MHC-molecule can be recognised by the T-cells. The MHC-molecules of the human are named human leukocyte antigens (HLA).

The treatment of cancerous diseases by an immunotherapy which is antigen specific and based on T-cells, in the past has proven to be successful.

The triggering of a specific CTL-response that is directed against a tumour is dependent from the identification of MHC-class I-ligands that are derived from tumour-associated antigens (TAA). Such tumour-associated antigens can be exclusively present in malign (maliciously transformed) cells, for example as a product of mutated genes. Other important classes of tumour-associated antigens are tissue-specific structures, such as, for example, the melanocyte differentiation antigens. A third class of tumour-associated antigens represent proteins that are over-expressed in tumours.

The methods for identifying and characterisation of TAA that are the basis for a therapeutic vaccine are on the one hand based on the stimulation of CTL or antibodies that are already present in the patients. This immunological approach is combined with either an analysis of the gene expression profile or with a mass-spectrometric sequencing of the identified gene (see van the Bruggen et al., 1991, A gene encoding an antigen recognised by cytolytic T lymphocytes on a human melanoma, Science 254:1643-1647, and Cox et al., 1994, Identification of a peptide recognised by five melanoma-specific human cytotoxic T cell lines, Science 264:716-719). Methods for identifying TAA that are based on the comparative analysis of the transcription profile of tumourous and normal tissue are, for example, the use of regular DNA-chip-technology and methods for hybridising of messenger-RNA from the tissue samples that are to be compared.

Celis et al., 1994, Induction of anti-tumour cytotoxic T lymphocytes in normal humans using primary cultures and synthetic peptide epitopes, Proc. Natl. Acad. Sci. USA 91:2105-2109, used a method that is based on the prediction of MHC-class I-ligands that are derived from a TAA, and wherein these predicted ligands are subsequently experimentally confirmed as T-cell-epitopes.

The disadvantage of these strategies, that necessarily require the availability of T-cells from patients, is the fact that the experimental use and cultivation is very complex.

Schirle et al., 2000, Identification of tumour-associated MHC class I ligands by a novel T-cell independent approach, Eur. J. Immunol. 30:2216-2225, describe a method that is independent from T-cells and wherein the prediction of MHC-class I-ligands is combined with the specific search for the predicted peptide-ligands in complex peptide-mixtures, wherein the peptides are identified by coupling of high-sensitive capillary liquid-chromatography with mass-spectroscopy (LC-MS).

Young et al., 2001, Expression profiling of renal epithelial neoplasms: a method for tumour classification and discovery of molecular markers, Am. J. Pathol., 158:1639-1651, showed that with the aid of analyses using DNA-chip-technology, a large number of TAAs can be identified from single tumours. MHC-class I-ligands that are derived from over-expressed, selectively, or exclusively expressed proteins therefore represent potential targets for an elimination of tumours based on CTL. Mathiassen et al., 2001, Tumour-associated antigens identified by mRNA expression profiling induce protective anti-tumour immunity, Eur. J. Immunol. 31:1239-1246, could show that in the model-organism mouse it is possible to produce an effective vaccine using the combination of gene expression analysis and epitope prediction.

The disadvantage of the epitope-prediction is based on the fact that already for a small number of TAAs a very large number of possible MHC-class I-ligands is determined, from which the majority in fact is not presented by MHC-class I-molecules at all, due to which the majority of the now predicted epitopes are incapable to trigger a CTL-based elimination of tumours.

Weinschenk et al., 2002, Integrated functional genomics approach for the design of patient-individual antitumor vaccines, Cancer Res. 62:5818-5827, show that by the combination of a gene expression analysis with the MHC-class I-ligands of a tumour that were isolated and analysed by liquid chromatography and mass spectroscopy into one method, selectively candidates for the selection of therapeutic vaccines can be determined. The big advantage in contrast to the exclusive use of gene expression analysis or mass spectroscopy is based on the fact that MHC-class I-ligands are determined from a complex mixture of peptides that are particularly suitable as immune reactive peptides due to the fact that they are in fact presented by MHC-class I-molecules as well as are derived from genes that are exclusively, selectively, or particularly strong expressed in the tumour.

The inventors of the present application have now realised that one disadvantage of the combined method of gene expression analysis and mass spectroscopy is based on the fact that peptides that trigger a CTL-response that is directed against MHC-class I-ligands of TAA that peptides that are presented strongly on the tumour and weakly on the normal tissue can not be reliably identified. It is therefore an object of the present invention to provide a novel method, by which selectively and in a simple fashion immune reactive peptides can be identified that trigger a CTL-response that is directed against MHC-class I-ligands of TAA that are highly presented strongly on the tumour and weakly on the normal tissue.

The inventors have realised that this object is solved if, for the identified peptide, the amount ratio of the peptide that is in fact presented by MHC-class I-molecules between tumour tissue and normal tissue or between accordingly transfected or infected cells and not transfected or infected cells is determined.

Therefore the method according to the invention for identifying and quantifying tumour-associated peptides comprises the following steps:

providing a first sample of tissue or cells,
providing a second sample of tissue or cells having the identical amount by weight or cellular count as the first sample,
obtaining peptides from the first and the second sample,
separately, chemically identically modifying the peptides from both samples in order to generate different physical characteristics in the peptides from the different samples,
mixing of the so modified peptides from both samples, determining the amino acid sequences of the peptides, and
determining the relative ratios of the amounts of peptides having identical sequences from both samples based on the different physical characteristics,
wherein preferably the peptides from both samples are chemically modified by using at least two different stable isotopes of the same element.

The object is therefore solved according to the invention by a method for identifying and quantifying tumour-associated peptides, wherein first for obtaining the peptides at least two different sources (tumour- and normal tissue or accordingly transfected cell lines) of the same amount by weight or cellular count are provided, and then the peptides from the different sources are separately from each other chemically modified in the same manner by using at least two different stable isotopes of the same element, the so modified peptides are then mixed and subsequently isolated, preferably by chromatographic methods, and the amino acid sequences of the peptides are determined, wherein the determination of the correlation of the relative ratios of the amounts of peptides having the identical sequence from different samples takes place on the basis of the stable isotope used in the chemical modification.

For this, the peptides are isolated according to standard protocols, for example by using a monoclonal antibody, such as the W6/32, which is specific for HLA-class-I-molecules.

In order to ensure that starting material in the same amount (weight in case of tissue) or cell count from both sources is used, additionally a normalisation can be performed using, for example, a peptide or other marker that is present both in tumour and normal tissue.

Furthermore, the invention relates to peptides that are identified according to the novel method, and to a tumour-associated peptide having an amino acid sequence that is selected from the group consisting of SEQ-ID No. 1 to 36 of the accompanying sequence protocol, wherein the peptide has the ability to bind to a molecule of the human major histocompatibility-complex (MHC) class-I.

In addition, the invention relates to the use of the peptides or the nucleic acid molecules encoding the peptides for producing a medicament, and for the treatment of tumourous diseases and/or adenomatous diseases.

A method according to the invention for identifying and quantifying tumour-associated peptides comprises the following steps:

a) providing a sample from tumourous tissue and a sample from corresponding healthy tissue or accordingly transfected or infected cell lines, wherein both samples exhibit identical amounts per weight or cellular counts,
b) isolating peptides from the sample from tumourous tissue,
c) isolating peptides from the sample from corresponding healthy tissue,
d) chemically modifying the peptides obtained in step (b) with a chemical group that contains a stable isotope of an element from the periodic system of elements (for example deuterium, $^2$D),
e) chemically modifying the peptides obtained in step (c) with a chemical group that contains a second stable isotope of the element from the periodic system of elements used in step d) (for example regular hydrogen, $^1$H),
f) mixing of the chemically modified peptides obtained from steps (d) and (e),
g) separating the peptides obtained from step f) by a chromatographic method,
h) identifying and determining of peptides having identical amino acid sequences, and the amount ratio of chemically modified peptides having identical amino acid sequences from step (g),
i) identifying tumour-associated peptides that are suitable, preferably particularly suitable, for the combination into a therapeutic vaccine, based on the data obtained from step (h).

The inventors have realised that by the method for determining the differences in the amount ratios of peptides between tumour tissue and normal tissue being preferably based on mass spectroscopy and differential chemical modification, peptides can be identified that are particularly suitable for the assembly of therapeutic vaccines.

It is therefore possible with the method according to the invention to identify peptides that are suitable for the individual assembly of, for example, a personalised mixture of tumour-associated peptides for an individual patient, wherein the peptides then can trigger a selective CTL-response that is in agreement with the individual need of a patient.

This method—after receipt of patient samples—can be performed systematically and efficiently, for example, by large laboratories, which, after identification of suitable peptides, transmit their sequences to the clinics that are the sites of treatment, where the peptides that are then synthesised can be formulated as therapeutic vaccines. Nevertheless, it is also possible that a laboratory performs the identification together with the pharmaceutically acceptable production, formulation, and provision of the tumour-associated peptides that are suitable for the respective patients.

In addition, the systematic and regular use of the method can lead to a commercial exploitation of suitable tumour-associated peptides being frequently found as MHC-class I-ligands in the form of pre-formulated medicaments.

The novel method can be employed in the context of a pure service as well as in connection with the production, formulation, and provision, for a single patient as well as for the exploitation by companies of the pharmaceutical industry in a suitable industrial scope.

In a preferred embodiment, the peptides that are isolated in the steps (b) and (c) are MHC-class I-ligands.

Only peptides that are bound to MHC-molecules can trigger a CTL-immune reaction. Peptides that are derived, for example, from over-expressed genes in a tumour but are not bound to MHC-molecules, do not trigger a CTL-immune reaction. Thus, not all, for example those peptides that have only been determined by prediction of epitopes, are indeed suitable for triggering an immune reaction.

In a preferred further embodiment, step (d) is performed by means of the guanidination of the ε-amino group of a lysine residue of a peptide by chemical reaction of peptides with O-methyl iso-urea-hemisulfate, and the nicotinylation of the α-amino group by chemical reaction of peptides with $^2D_4$-nicotinyl-amino-hydroxy-succinimide ($^2D_4$-NicNHS). The guanidination of the ε-amino group of a lysine residue of peptides is, for example, described in Beardsley et al., 2002, Optimization of guanidination procedures for MALDI mass mapping, Anal. Chem. 74:1884-1890. The nicotinylation of the α-amino group of peptides is, for example, described in Munchbach et al., 2000, Quantitation and facilitated de novo sequencing of proteins by isotopic N-terminal labelling of peptides with a fragmentation-directing moiety, Anal. Chem. 72:4047-4057.

In a preferred further embodiment, step (e) is performed by means of the guanidination of the ε-amino group of a lysine residue of a peptide by chemical reaction of peptides with O-methyl iso-urea-hemisulfate, and the nicotinylation of the α-amino group by chemical reaction of peptides with $^1H_4$-nicotinyl-amino-hydroxy-succinimide ($^1H_4$-NicNHS).

In a preferred further embodiment, in steps (g) and (h) the analysis is performed by means of coupled liquid chromatography and mass spectroscopy methods. By means of this technique the individual chemically modified peptides can be accurately and efficiently determined, and with high throughput. The use of mass spectroscopy for determining chemically modified peptides is, for example, described in Munchbach et al., 2000, Quantitation and facilitated de novo sequencing of proteins by isotopic N-terminal labelling of peptides with a fragmentation-directing moiety, Anal. Chem. 72:4047-4057. The identification of peptides from tumourous tissue is, for example, described in Weinschenk et al., 2002, Integrated functional genomics approach for the design of patient-individual antitumor vaccines, Cancer Res. 62:5818-5827.

In another preferred embodiment, an additional step is performed following step (h), wherein the reactivity of leukocytes from the peripheral blood, preferably T-lymphocytes, against the peptides as defined by step (h) is tested.

In a preferred embodiment, the reactivity of peripheral leukocytes against the peptides as defined by step (h) is tested by measuring the γ-interferon-mRNA and/or cytokine-mRNA produced by the leukocytes.

Using the determination of γ-interferon-mRNA and/or cytokine-mRNA, it is possible to accurately determine the specific reactivity of leukocytes, preferably of T-lymphocytes, against the peptide antigens. Both compounds are secreted by activated T-lymphocytes following their activation through respective peptides that are present on the cellular surfaces and are bound to MHC-molecules. This additional step allows for the possibility to more selectively identify candidates from the already identified peptides.

In another preferred embodiment of the method, an additional step is performed following step (h), wherein the existence of specific T-lymphocytes is determined.

Using this method it is possible to specifically find out, in as far and to what extent already T-lymphocytes against the isolated and the identified peptides are present in patients. By means of this step it is possible to use only those peptides as therapeutic vaccine for which already T-lymphocytes are present in patients. The peptides can then be employed in order to activate these specific T-lymphocytes.

In another preferred method the determination of the existence of specific T-lymphocytes takes place by labelling of the leukocytes with reconstituted complexes of MHC-molecules and antigenic peptide.

In this method, the so-called tetramer-technology is used. How to obtain such reconstituted complexes ("tetramers") and their use is, for example, described in Altman et al., 1996, Phenotypic analysis of antigen-specific T-lymphocytes, Science 274:94-96.

In another preferred method, the specific T-lymphocytes from peripheral blood of patients are activated with reconstituted complexes from MHC-molecules and antigenic peptides that are bound to a synthetic surface together with the molecule CD28. This method is, for example, described in Walter et al., 2003, Cutting Edge: predetermined avidity of human CD8 T cells expanded on calibrated MHC/anti-CD28-coated micro spheres, J. Immunol. 171:4974-4979.

In another aspect, the invention relates to immunoreactive peptides that are identified and/or produced using the method according to the invention.

Following identification, these peptides can be selectively and specifically produced, i.e. synthesised chemically, in vitro or in vivo.

It will be understood that, in doing this, at least one amino acid can be replaced by another amino acid having similar chemical characteristics, at least one additional amino acid can be present at the N- or C-terminus, at least one amino acid can be deleted, and/or at least one amino acid can be chemically modified, without that the immunoreactive characteristics of the peptides disappear.

The invention furthermore relates to a pharmaceutical composition containing one or more of the peptides that have been identified and/or produced according to the method of the invention.

This composition can be used, for example, for the parenteral application, for example by subcutaneous, intradermal or intramuscular application. For this, the peptides are dissolved or suspended in a pharmaceutical carrier, furthermore, the composition can contain excipients, such as, for example, buffers, binding agents, assembling agents, etc. An extensive presentation of excipients that can be used in such a composition is described, for example, in A. Kibbe, 2000, Handbook of Pharmaceutical Excipients, 3. Ed., American Pharmaceutical Association and Pharmaceutical Press. The peptides can also be administered together with immune stimulating substances, such as, for example, cytokines. An extensive presentation of immune stimulating substances that can be applied together with peptides is, for example, described in Ribas et al., 2003, Current developments in cancer vaccines and cellular immunotherapy, J. Clin. Oncol. 21:2415-2432.

In accordance with the invention, the peptides can be used for the treatment of tumourous diseases and for the production of a means for the treatment of tumourous diseases.

The tumourous diseases to be treated encompass renal, lung, colon, stomach, pancreatic, breast, prostate, ovarian and/or skin cancer. This listing of the tumourous diseases shall be meant as exemplary, and shall not limit the fields of uses.

Furthermore, the peptides can also be used for evaluating the progress of a therapy in tumourous diseases.

In addition, the peptides can be used in other vaccinations or therapies for the evaluation of the course of a therapy. Thus, the peptides according to the invention can not only be used therapeutically but also diagnostically.

In another embodiment, the peptides are used for the production of antibodies.

Polyclonal antibodies can be obtained in a common manner by immunising animals through injection of the peptides, and subsequent purification of the immunoglobulins from the blood of the immunised animals.

Monoclonal antibodies can be produced following standard protocols, such as, for example, described in Methods Enzymol., 1986, Hybridoma technology and monoclonal antibodies, 121:1-947.

Topecific monoclonal antibodies can be produced following standard protocols, such as, for example, described Tomlinson et al., 2000, Methods for generating multivalent and topecific antibody fragments, Methods Enzymol. 346:461-479.

In another aspect, the invention relates to nucleic acid molecules that encode for the peptide that has been isolated using the method according to the invention.

The nucleic acid molecules can be DNA- or RNA-molecules and can, optionally, also be used for the immunotherapy of cancerous diseases.

According to the invention, the nucleic acid molecules can also be present in a vector.

Furthermore, the invention relates to a cell that has been genetically modified with the nucleic acid molecule in such a manner that the cell produces a peptide as identified according to the invention.

This invention furthermore relates to a method for producing a tumour-associated peptide, wherein a peptide is identified based on the method as described, and said identified peptide is chemically synthesised, in vitro or in vivo.

Peptides can be produced by chemical reaction of amino acids, for example, by the method according to Merrifield, which is described in Merrifield, 1963, J. Am. Chem. Soc. 85:2149-2154.

In vitro peptides can be produced, for example, in cell-free expression systems, in vivo peptides can be produced in prokaryotic and eukaryotic cells.

A preferred embodiment of the present invention is a method for producing a vaccine with the steps
(a) performing the method as described above,
(b) producing the tumour-associated peptides identified in step (i), and
(c) formulating the tumour-associated peptides produced in step (j).

The invention furthermore relates to a diagnostic method, wherein the novel method is performed, and the presence and/or the amount ratio of a peptide is used as a diagnostic marker, a method for treating a pathological condition, wherein an immune response against a protein of interest is triggered, wherein a therapeutically effective amount of at least one peptide found according to the novel method is administered, as well as an electronic storage medium containing the amino acid sequence of at least one peptide according to the invention and/or the nucleic acid sequence of a nucleic acid molecule encoding for a peptide according to the invention.

It will be understood that the features as indicated above and the features that are to be further explained below can be used not only in their combination as explicitly indicated herein but also in other combinations or alone without departing from the scope of the present invention.

In the following, embodiments of the invention are presented and explained in the figures and the example.

Figure 3:
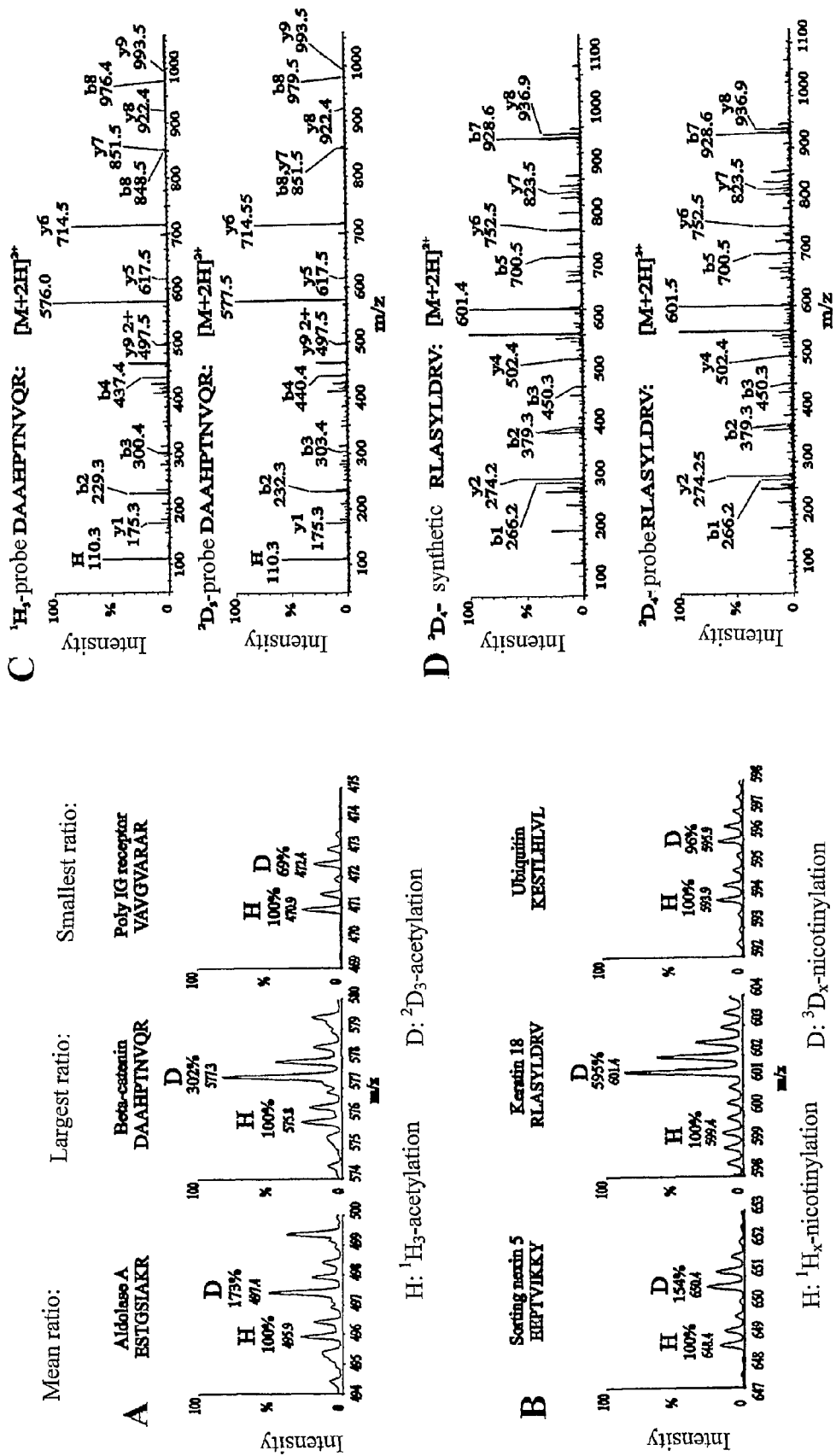
Figure 4:
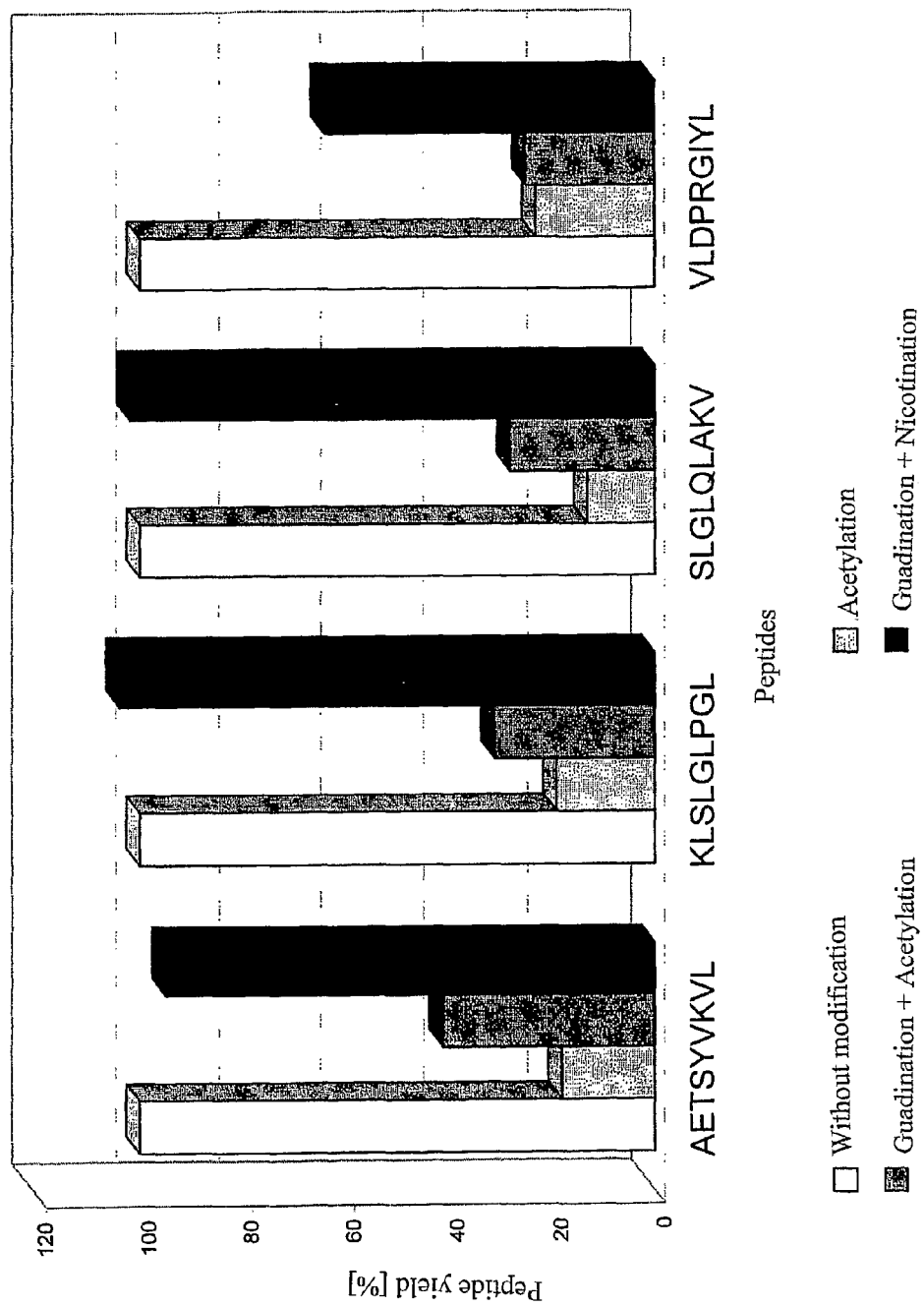

FIG. 3 shows a comparative quantification of antigenic peptides from two different sources, wherein in (A) a mass spectroscopic analysis of the relative amount ratios of three different peptides from two tissue samples (colon cancer sample, sample of healthy tissue from the same patient) is shown. The peptides isolated from the colon cancer sample were $^2D_3$-acetylated. The peptides isolated from the sample of healthy tissue were $^1H_3$-acetylated. (B) shows a mass spectroscopic analysis of $^1H_4$-nicotinated/guadinated Awells-cells, and Awells-cells transfected with keratin 18, and $^2D_4$-nicotinated/guadinated Awells-cells. (C) shows the determination of the amino acid sequences of an $^1H_3$-acetylated peptide with the amino acid sequence DAAHPTNVQR (SEQ ID NO: 12) and of a $^1D_3$-acetylated peptide with the amino acid sequence DAAHPTNVQR (SEQ ID NO: 12) by fragmentation;

FIG. 4 shows yields of peptides that have been chemically modified in four different ways. Four peptides with the amino acid sequences AETSYVKVL (SEQ ID NO: 38), KLSLGLPGL (SEQ ID NO: 39), SLGLQLAKV (SEQ ID NO: 40) and VLDPRGIYL (SEQ ID NO: 41) were used in a mixture in equimolar amounts, and were subsequently for the purpose of the comparative examination of the three strategies for chemical modification either acetylated, or acetylated and guadinated, or guadinated and nicotinated. After finalization of the chemical reaction for modification of the reference peptides, these were mixed with the initially used non-modified peptides in order to allow for a comparison in the following analytic step. The comparative evaluation was performed by analysis with nano-electrospray-ionisation-mass spectrometry (nano-ESI-MS).

EXPERIMENTAL METHODS

Patient Sample

A sample from a patient that had histologically confirmed colon cancer was obtained from the department for general surgery of the Universitatsklinikum der Universität Tübingen. The patient (in the following designated with CCA129) had the HLA-class-I-type HLA-A*01, HLA-A*68, HLA-B*08, HLA-B*44.

Cell Line

The Awells cell line was used (European Collection of Cell Cultures, Porton Down, Salisbury, United Kingdom), which has the HLA-class-I-type HLA-A*02, HLA-B*44.

Keratin 18-Transfected Cell Line

The Awells cell line was stably transfected with the DNA-sequence for human keratin 18 according to standard protocols. For this, the cDNA encoding for human keratin 18 was subcloned by using the TOPO TA Cloning Kit (Invitrogen, Karlsruhe, Germany). The subsequent cloning took place between the restriction-endonuclease-cleavage sites of EcoR I and Not I of the plasmid vector pcDNA3-Ii, in frame with the Ii-sequence. The transfection of the Awells-cells was performed by means of electroporation, whereupon stable transfectants were selected and held in culture.

Isolation of the HLA-Class-I-Bound Peptides

The processing of the tissue sample that were shock frosted in liquid nitrogen after surgical removal was performed as already described in Schirle et al., Identification of tumour-associated MHC class I ligands by a novel T cell independent approach, 2000, European Journal of Immunology, 30:2216-2225. The peptides were isolated following standard protocols, and in particular by using the monoclonal antibody W6/32, which is specific for HLA-class-I-molecules. Barnstable et al., Production of monoclonal antibodies to group A erythrocytes, HLA and other human cell surface antigens—new tools for genetic analysis, 1978, Cell, 14:9-20, describes the production and use of this antibody.

Acetylation of Peptides

10 µl $^1H_6$-acetyl-anhydride or $^2D_6$-acetyl-anhydride (50% solution per volume in methanol) were added to 100 µl peptide mixture (amount of peptides in the mixtures: between 2 nmole and 200 pmole) in a 50% methanol/water-mixture (per volume). The chemical reaction took place during 15 minutes at room temperature. The reaction was stopped by the addition of 1.1 µl formic acid. Subsequently, identical volumes from both preparations were taken and mixed.

Guanidination of Peptides

To a peptide mixture from tumour tissue (CCA129), or keratin-18-transfected or non-transfected Awells-cells (amounts of peptides in the mixtures: between 2 nmole and 200 pmole) in citrate-buffer (50 mM citrate, pH 3.0) 0.25% trifluoro-acetic acid (TFA, per volume) was added, subsequently the pH of the mixture was adjusted with 200 µl sodium hydroxide (10 M solution) to 10.5. After addition of 1 ml O-methyl-iso-urea-hemisulfate-solution (2.5 M in water), the reaction mixture was incubated for 10 minutes at 65° C. (water bath). The reaction was stopped by the addition of 200 µl formic acid.

Nicotinylation of Guanidinated Peptides

The peptide mixture from tumour tissue (CCA129) that was chemically modified by guanidination, or keratin-18-transfected or non-transfected Awells-cells were loaded on a chromatographic column of the type "reversed phase C-18 microcolumn" (Agilent Technologies hydrophobic XGSXB), and washed with 0.5 ml water. The peptide that was bound to the material of the column was then left on the column, and was nicotinylated by chemical reaction at room temperature by slowly adding 1 ml of freshly prepared $^1H_4$- or $^2D_4$-nicotinyl-N-hydroxysuccinimide-ester (sodium phosphate buffer 50 mM; pH 8.5). Following this, for a second time 1 ml of freshly prepared $^1H_4$- or $^2D_4$-nicotinyl-N-hydroxysuccinimide-ester is slowly applied through the chromatographic column that is loaded with the peptide mixture. Then, hydroxylamine was applied through the column in order to remove again unwanted modifications of tyrosine residues by nicotinyl groups. Finally, the chromatographic column was washed with water, before the peptides were eluted from the column with 100 µl of a 50% acetonitrile/water-mixture (per volume).

Offline-High Performance Liquid Chromatography—(HPLC—) Separation of Peptide Mixtures Mixtures of peptides that were chemically modified in this way were mixed in equimolar ratios, and reduced in their volume to approx. 100 µl by vacuum-centrifugation. The reduced mixtures were diluted with 400 µl water with 0.08% TFA (per volume), before they were loaded by automatic sample injection on a "reversed phase"-chromatographic column of the type µRP SC C2/C18, 100 mm×2.1 mm, Amersham-Pharmacia, Freiburg, Germany) attached to a SMART-HPLC-system (Amersham-Pharmacia, Freiburg, Germany). For chromatographic separation and elution of the peptides that were bound to the material of the column, a binary gradient out of two mixtures of solvents A and B was used. Solvent mixture A contained 0.1% TFA (per volume) in water. Solvent mixture B contained 0.08% TFA and 80% acetonitrile (both per volume) in water. The binary gradient started with 90% solvent mixture A and 10% solvent mixture B, and took a linear course to a mixing ratio of 40% solvent mixture A and 60% solvent mixture B. The eluate was collected in fractions having a volume of 150 µl per each fraction. Prior to the mass spectrometric evaluations of the chromatographically separated peptides the collected fractions were completely dried by vacuum centrifugation, and subsequently dissolved again in a mixture of 50% methanol, 49.9% water and 0.1% formic acid.

Microcapillary-Liquid Chromatography-Mass Spectrometry

These peptide mixtures were analysed with the aid of a reversed-phase-HPLC-system ("reversed phase Ultimate HPLC System, Dionex, Amsterdam, The Netherlands) that was attached to a hybrid-quadropol-mass spectrometry device ("orthogonal acceleration time of flight mass spectrometer", Micromass, Manchester, United Kingdom) equipped with a micro-elektrospray-ionisation source. For this, the sample material is first desalted and pre-concentrated on a C18-pre-column having the sizes 300 µm×5 mm (LC Packings, Amsterdam, the Netherlands). The solvent and the sample were added with a speed of 2 µl per minute using a syringe-pump (Harvard Apparatus, Inc.) with a fitted 100 µl-syringe (1710 RNR, Hamilton). The pre-column that is loaded with the peptide-mixture is positioned in direction of the flow in front of a silica-column (75 µm×250 mm, Dionex, Amsterdam, The Netherlands) which is attached to the "reversed phase Ultimate"-HPLC-system and loaded with C18-reversed-phase material (5 µm, Dionex, Amsterdam, The Netherlands). For eluting the bound peptide, a binary gradient was applied during a period of 120 minutes which started with 15% solvent A (4 mM ammonium acetate in water, pH 3.0) and 85% solvent B (2 mM ammonium acetate in a mixture per volume of 80% acetonitrile and 20% water, pH 3.0), and led to a mixing ratio of 40% solvent A and 60% solvent B. The velocity of the flow-through during the elution of the peptides was reduced by the Ultimate split-system (Dionex, Amsterdam, The Netherlands) to approx. 300 µl per minute. The eluate was introduced by a gold-coated glass capillary (PicoTip, New Objective, Cambridge, Mass., U.S.A.) into the micro-ESI-source. The integration time for the "time of flight"-analysis (TOF analyser) was set to 1 second, the retention time between two analyses was 1/10 second. The ratio of chemically modified peptides with deuterium—($^2D$-) atoms to peptides that are based on the identical amino acid sequence with regular hydrogen ($^1H$—) atoms were determined by comparing the relative heights of the peaks (measured peaks of the signals as generated from the mass spectrometric analysis).

The online-fragmentation of peptides for determining the amino acid sequence (HPLC-MSMS) was performed with an integration time for the "time of flight"-analysis (TOF analyser) of 4 seconds and a retention time between two analyses of 1/10 seconds and, apart from this, was performed as described. During the process, the online-fragmentation of the $[M+H]^+$ and $[M+H]^{2+}$-ions was automatically switched between the HPLC-MS- and the HPLC-MSMS-modus. The spectra resulting from the mass spectrometric analyses were analysed manually. NCBInr and EST were used as databases with the use of MASCOT software available from Matrix Science Ltd. (London, U.K.).

In another preferred embodiment, for small sample volumes, for a further reduction of the rate of flow-through for the loading of the sample onto the micro-ESI-source, instead of a HPLC-system also metal coated glass capillaries (Proxeon, Odense, Denmark) can be used. Thereby, flow-rates of 20 nl per minute to 50 nl per minute are possible. In this embodiment, the ratio of chemically modified peptides with deuterium—($^2$D-) atoms to peptides that are based on the identical amino acid sequence with regular hydrogen—($^1$H—) atoms is determined by comparison of the relative heights of the peaks (measured peaks of the signals as generated from the mass spectrometric analysis) and the relative mathematically integrated areas of the peaks. Also in this embodiment, the fragmentation of peptides in the HPLC-MSMS-modus is possible. This is performed with collision energies of 30-60 eV for [M+H]$^+$-ionised fragments and 20-30 eV for [M+H]$^{2+}$-ionised fragments. For this embodiment, the integration time for the time of flight-analysis (TOF analyser) is 1 second, and between two analyses a retention time of $^1$/$_{10}$ second is introduced.

Results

Figure 1:
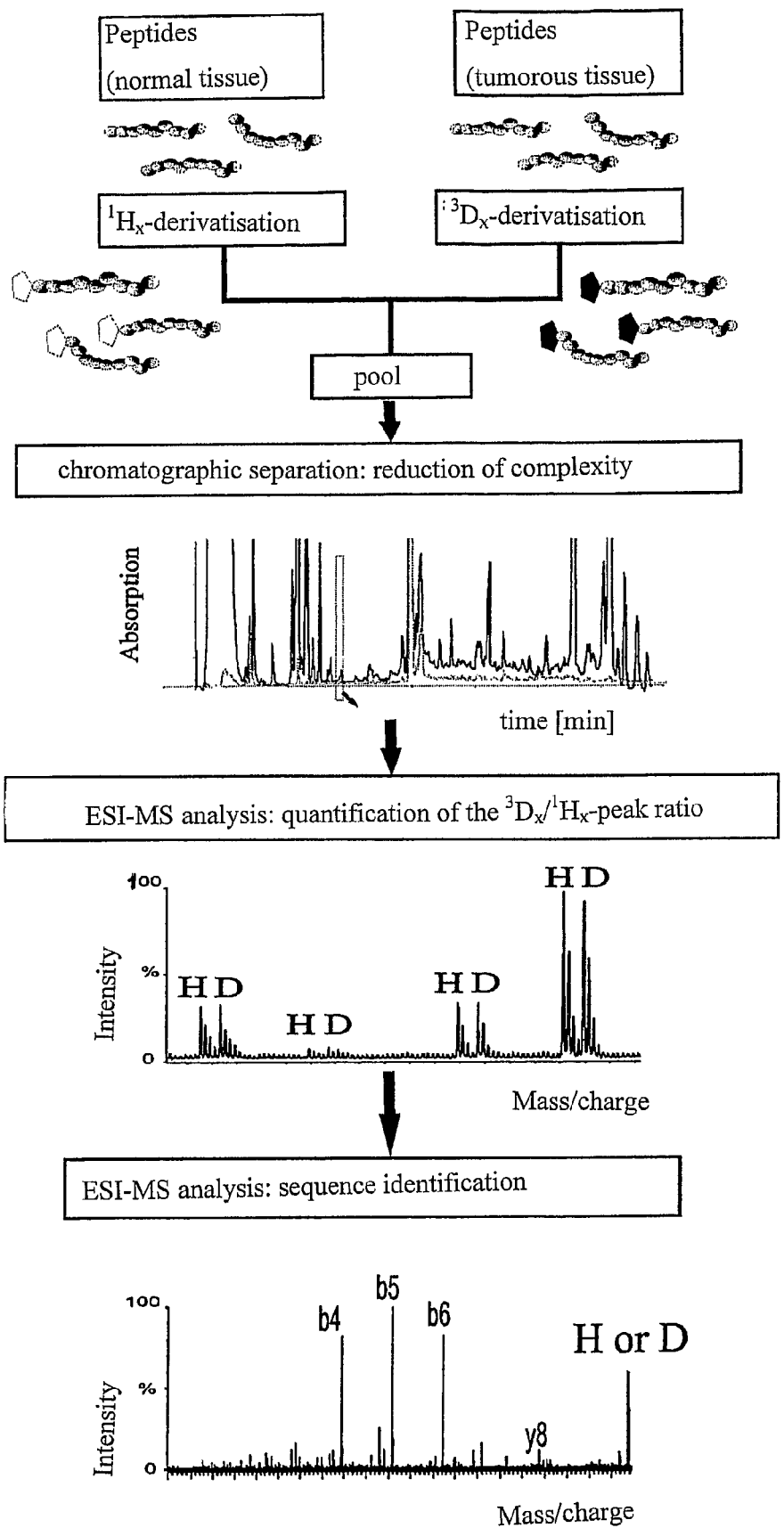
FIG. 1 shows a summary of the method for identifying and quantifying tumour-associated peptides according to the invention.

FIG. 1 depicts the general principle of the differential determination and identification of MHC-class-I-bound peptides. In this Method peptides from two different sources are treated with reactive chemical groups, that can be differentiated based on the presence or absence of certain hydrogen-species (light hydrogen: $^1$H; heavy hydrogen: $^2$D), without that the physical characteristics that are achieved by the different hydrogen-isotopes being used for a separation have a detectable effect on the chemical characteristics of the modified peptides. The peptide-derivatives that are generated by the chemical modification are combined, i.e. mixed or assembled, and separated by chromatography ("offline"-HPLC or "online"-HPLC-MS) according to their hydrophobicity or hydrophilicity, respectively that is based on their primary amino acid sequence. The signal intensity of the specific mass/charge-signals as determined by the subsequent mass spectrometric analysis is the indicator for the relative ratio per amount between peptides that are based on the identical primary amino acid sequence that were obtained from different sources. The use of the tandem-MSMS-methods together with the use of databases provides additional information about the amino acid sequence of the peptide that is present for the individual case.

The acetylation of MHC-class-I-ligands represents a fast and simple method for the chemical modification of peptides. The acetylation of peptides was optimised experimentally by using synthetic peptide mixtures. The peptides were completely acetylated at the amino terminal end after 15 minutes reaction time (as described).

Use of $^2$D$_6$- and $^1$H$_6$-Acetanhydride for the Acetylation Allows for the Differential Quantification of Peptides.

Figure 2:
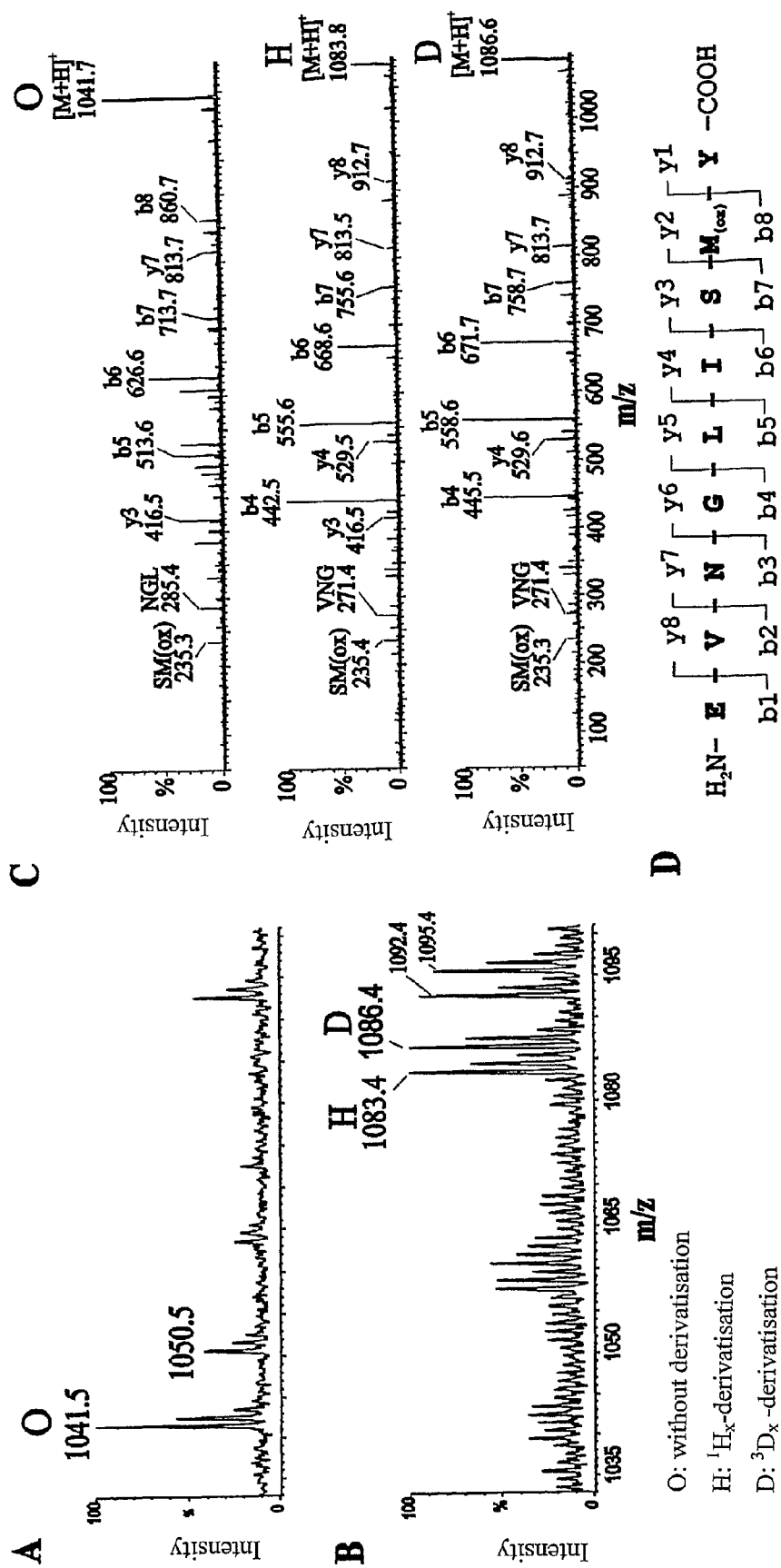
FIG. 2 shows the mass spectroscopic analysis of (A) non-modified and (B) $^1H_3/^2D_3$-acetylated peptides. (C) Mass spectroscopic analysis of a peptide mixture that, as an example, contains the non-modified peptide as well as the $^1H_3$-acetylated peptide, and the $^2D_3$-acetylated peptide with the amino acid sequence EVNGLISMY (SEQ ID NO: 37); (D) explains the nomenclature used in FIG. 2.

MHC-class-I-bound peptides were obtained as described from MGAR-cells for demonstrating the feasibility, separated in two partial samples with the same volume, and acetylated as described with $^2$D$_6$- and $^1$H$_6$-acetanhydride, respectively. Following the end of the chemical reaction, the partial samples were again mixed in equimolar ratios, and the relative ratios between $^2$D$_3$- and $^1$H$_3$-acetylated peptides were determined. As an example, FIG. 2 shows the $^2$D$_3$- and $^1$H$_3$- variants of a peptide with the amino acid sequence EVNGLISMY (molecular weight without chemical modification: 1040.5 Da). The peptide EVNGLISMY represents a fragment from the "U5 snRNP-specific protein". The relative ratio between $^2$D$_3$- and $^1$H$_3$-variants ($^2$D$_3$/$^1$H$_3$-ratio) of EVNGLISMY as determined was 1.0. For 15 additional peptides that were eluted from the same MGAR-cells and were detected by mass spectrometry as single or twofold charged ions, the $^2$D$_3$/$^1$H$_3$-ratio in the arithmetic mean was 1.01. The standard deviation (SD) was ±0.13 (table 1). In addition to enabling a determination of the relative parts of peptides that are based on the identical amino acid sequence from two or several different sources the acetylation of peptides, due to the shift of the b-series-ions in the order of 3 Da of $^2$D$_3$-acetylated compared to $^1$H$_3$-acetylated peptides, also leads to a simplification of the analysis of the corresponding mass spectrograms (FIG. 2C). b-Series-ions in general are ionised fragments of chemically modified as well as non-modified peptides that contain at least the amino acid residue positioned at the amino terminus in the amino acid primary sequence. In contrast to the b-series-ions, y-series-ions in general are ionised fragments of chemically modified as well as non-modified peptides that contain at least the amino acid residue positioned at the carboxy terminus in the amino acid primary sequence.

The disadvantage of the acetylation of peptides is, that the ionisation by introducing the acetyl residue at the amino terminal end of the peptide can lead to the loss of a positive charge compared to a peptide with an intact N-terminus. Due to the fact that, in general, peptides having several charges can be better detected in mass spectrometry than single charged ones, the acetylation leads to a loss of sensitivity. The experiments as performed also showed that additionally an acetylation of the ε-amino group of lysine residues can occur. This acetylation of the ε-amino group of lysine residues also leads to the fact that, due to the ionisation, a positive charge less than in the peptide being not chemically modified by acetylation can be created. Nevertheless, the concomitant loss of sensitivity holds true to the identical extent for the identical primary amino acid sequence as the basis of the peptides from the different sources used, such that there is no detectable influence of the inner ratio between the respective signals of the, in one case $^2$D$_3$- and in the other case $^1$H$_3$-acetylated peptides having identical sequences.

Identifying of MHC-Class-I-Bound Peptides from Tissue Samples of Colon Tumour and Tissue Samples of Normal Tissues Surrounding the Tumour, by using $^2$D$_3$- and $^1$H$_3$-Acetylation and Comparing the Relative Amounts of the MHC-Class-I-Bound Peptides in a Mass Spectrometric Analysis on the Basis of Electrospray-Ionisation-Mass Spectrometry (ESI-MS).

Peptides were isolated as described from MHC-class-I-molecules of a colon cancer sample (CCA129) and from MHC-class-I-molecules of a sample of the surgically removed normal tissue surrounding the tumour, and subsequently chemically modified by $^2$D$_3$—(tumour) and $^1$H$_3$—(normal tissue) acetylation. Following the chromatographic separation of the modified peptides by microbore-HPLC, 19 peptides were identified by nano-ESI-MS as described. Out of these 19 peptides, for 17 the relative comparative amount ratio between specific peptides of the tumour tissue sample to the peptides of the sample of normal tissue that are based on the identical amino acid sequence could be determined as described. The majority of the identified peptides was present in similar amounts ($^2$D$_3$/$^1$H$_3$-ratios between 1.07 and 2.42) in both samples as examined. In summary, the 1.7-fold amount of peptides was present in the tumour sample compared to normal tissue sample. Two peptides were over-represented in tumour tissue, one peptide was under-represented in tumour. The statistical evaluation of the results by using the "student's t-test" confirmed that only the two over-expressed and the single under-expressed peptide were positioned outside of a 99.99% confidence interval of 0.87 to 2.56.

The two peptides that were over-represented in tumour were derived from the human proteins ribosomal protein L24 and beta-catenin. Although few data with respect to a tumour association exist for the ribosomal protein L24, for the ribosomal protein L15 that is related to the ribosomal protein L24, a role in the development of oesophageal cancer was described by Wang et al., 2001, Cloning and characterisation of full-length human ribosomal protein L15 cDNA which was over-expressed in oesophageal cancer, Gene 263:205-209. In contrast, for beta-catenin, a function as oncogene that by transactivation switches on other oncogenes, such as, for example, the matrix-metalloproteinase MMP-7, was described by Ougolkov et al., 2002, Oncogenic beta-catenin and MMP-7 (matrilysin) cosegregate in late-stage clinical colon cancer, Gastroenterology 122: 60-71. A mutated beta-catenin-peptide was described by Robbins et al., 1996, A mutated beta-catenin gene encodes a melanoma-specific antigen recognised by tumour-infiltrating lymphocytes, Journal of Experimental Medicine 183:1185-1192, as target structure in connection with the human MHC-allele HLA-A*24 for CD8-positive, skin cancer infiltrating T-cells.

Improved Yield of MHC-Class-I-Bound Peptides after Chemical Modification of the Peptides by O-Methyl-Iso-Urea-Hemisulfate and Nicotinyl-N-Hydroxy-Succinimide-Ester (NicNHS).

The first-time and novel combination of two methods for chemical modification of peptides by combination of the uniform guanidination of ε-amino group of lysine residues in peptides by O-methyl-iso-urea-hemisulfate, and the nicotinylation of the α-amino group the peptides by NicNHS resulted in a clear improvement of the ionisation of peptides (FIG. 4). In order to simplify the desalting of the chemically modified peptides, the nicotinylation of the peptides is performed as described on a C18-chromatograpy column. The unwanted modification of the side chains of tyrosine residues caused by the nicotinylation could be removed again by treatment of the modified peptides with hydroxylamine. As an example FIG. 4 shows, based on the peptide having the amino acid sequence AETSYVKL, that the nicotinylation of the N-terminus influences the ionisation in way that results in a detection of nicotinylated peptides that is as good as with chemically non-modified peptides.

Identifying and Quantifying of MHC-Class-I-Bound Peptides from the Awells Cell Line and the Awells Cell Line Transfected with a Plasmid Containing the cDNA of the Human Keratin 18 by Guanidination and $^2D_4$-/$^1H_4$-Nicotinylation of the Peptides.

It was shown by Trask et al., 1990, Keratins as markers that distinguish normal and tumour-derived mammary epithelial cells, Proc. Natl. Acad. Sci. U.S.A., 87:2319-2323, that keratins are suitable as markers for distinguishing between tumour and healthy tissue. In order to identify novel MHC-class-I-bound peptides from human keratin 18, and in order to show the differential quantifying based on an exemplary tumour antigen, peptides were isolated from the non-transfected (Awells) and from the Awells-cell line (Awells Keratin 18) transfected with the plasmid as given. Subsequently, the isolated peptide-mixture was chemically modified as described by guanidination and $^2D_3$-, and $^1H_3$-nicotinylation, respectively. The chemically modified peptide mixtures were mixed, and examined by HPLC-MS-analysis as described. A second experiment was performed in the MSMS-modus, whereby the amino acid sequences of a total of 27 different peptides could be determined. All 27 peptides as found, with the exception of one peptide having a molecular weight of 1091.6 Da, were detected both in transfected as well as on non-transfected cells in amounts that were located within the confidence interval of 0.64 to 2.28 (statistic evaluation by using the "student's t-test"). For the peptide with a molecular weight of 1091.6 Da, the amino acid sequence RLASYLDRV was determined by the MSMS-analysis, which represents a fragment of the amino acid sequence of keratin 18. The MSMS-spectra that led to the identification of the peptide with the sequence RLASYLDRV are shown in FIG. 3D. For the peptide RLASYLDRV, no signal could be detected that could be correlated to a chemical modification of the primary sequence with a $^1H_3$-nicotinyl residue. This observation leads to the assumption that keratin 18 was exclusively expressed in the Awells keratin 18-cells. In contrast, the signal for the peptide RLASYLDRV with a $^2D_3$-nicotinyl residue was expressed six fold higher compared to background.

The described methods of the guanidination and nicotinylation of peptides by using the two hydrogen isotopes $^1H$ and $^2D$ for the first time allows for the rapid and exact determination of relative quantitative differences between peptides having the identical sequence from two or more different sources. By use of the methods for guanidination and nicotinylation of peptides on samples of tumour tissue and normal tissue of the same organ, or by use of said methods on cell lines that were transfected prior with nucleic acids encoding for oncogenes or other tumour-associated gene products, tumour-associated peptide antigens can be determined that are particularly suitable for the production of vaccines for cancer therapy.

Tables 1 to 3 summarise the above described results, table 4 shows the relationship of the peptides as identified with the protein-source and indicates the respective SEQ-ID No. from the sequence protocol, the sequence protocol shows the peptides according to the invention.

The invention claimed is:

1. A method for identifying and quantifying tumour-associated peptides, the method comprising the following steps:
   a) providing a sample from tumorous tissue and a sample from a corresponding healthy tissue, wherein both samples have identical amounts per weight or identical cellular counts;
   b) isolating peptides from the tumorous tissue sample, wherein isolating the peptides is performed with an antibody specific for HLA class I molecules;
   c) isolating peptides from the corresponding healthy tissue sample, wherein isolating the peptides is performed with an antibody specific for HLA class I molecules;
   d) chemically modifying the peptides obtained in step (b) with a chemical group that contains a first stable isotope of an element from the periodic system of the elements;
   e) chemically modifying the peptides obtained in step (c) with a chemical group that contains a second stable isotope of the element from the periodic system of the elements used in step d), wherein the first and second stable isotopes are different isotopes of the same element from the periodic system of elements;
   f) mixing of the chemically modified peptides obtained from steps (d) and (e);
   g) separating the peptides obtained from step f) by a chromatographic method;
   h) determining the amino acid sequence of the peptides;
   i) determining the relative ratio of the amount of peptides having identical amino acid sequences isolated from both the tumor and corresponding healthy tissue samples, using the difference of the first and second stable isotopes of the same element to determine the relative ratio;
   j) using the relative ratio determination in step (i) to identify tumor associated peptides; and
   k) testing reactivity of T lymphocytes against the tumor associated peptides to identify immunogenic tumor associated peptides, and wherein the peptide has the ability to bind to a molecule of MHC class-I.

2. The method according to claim 1 wherein deuterium ($^2$D) and regular hydrogen ($^1$H) are used as the first and second stable isotopes.

3. The method of claim 2 wherein the chemical modifications comprise guanidination of the ε-amino group of a lysine residue in the peptides with O-methyl-isourea-hemisulfate and nicotinylation of the α-amino group of the peptides with nicotinyl-N-hydroxy-succinimide-ester (NicNHS).

4. The method of claim 3, wherein the nicotinylation is either $^2$D$_3$- or $^1$H$_3$ nicotinylation.

5. The method of claim 3, further comprising treating of the modified peptides with hydroxylamine.

6. The method according claim 1, wherein in the chromatographic method comprises HPLC.

7. The method according to claim 1, wherein steps (h) and (i) are performed by mass spectrometric analysis.

8. The method according to-claim 1, wherein the testing of the reactivity takes place by the activation of peripheral T-lymphocytes by reconstituted complexes from antigen-presenting molecules and the peptides.

9. The method of claim 3, wherein the nicotinylation is either $^2D_4$- or $^1H_4$-nicotinylation.

* * * * *

SEQUENCE LISTING

<160> NUMBER OF SEQ ID NOS: 41

<210> SEQ ID NO 1
<211> LENGTH: 9
<212> TYPE: PRT
<213> ORGANISM: Homo sapiens

<400> SEQUENCE: 1

Thr Thr Glu Gln His Gly Ala Arg Tyr
1               5

<210> SEQ ID NO 2
<211> LENGTH: 8
<212> TYPE: PRT

-continued

<213> ORGANISM: Homo sapiens

<400> SEQUENCE: 2

Phe Thr Lys Val Lys Pro Leu Leu
1               5

<210> SEQ ID NO 3
<211> LENGTH: 9
<212> TYPE: PRT
<213> ORGANISM: Homo sapiens

<400> SEQUENCE: 3

Val Ala Val Gly Val Ala Arg Ala Arg
1               5

<210> SEQ ID NO 4
<211> LENGTH: 9
<212> TYPE: PRT
<213> ORGANISM: Homo sapiens

<400> SEQUENCE: 4

Asp Val Ser His Thr Val Val Leu Arg
1               5

<210> SEQ ID NO 5
<211> LENGTH: 9
<212> TYPE: PRT
<213> ORGANISM: Homo sapiens

<400> SEQUENCE: 5

Thr Leu Gly Asp Ile Val Phe Lys Arg
1               5

<210> SEQ ID NO 6
<211> LENGTH: 9
<212> TYPE: PRT
<213> ORGANISM: Homo sapiens

<400> SEQUENCE: 6

Asp Ile His His Lys Val Leu Ser Leu
1               5

<210> SEQ ID NO 7
<211> LENGTH: 9
<212> TYPE: PRT
<213> ORGANISM: Homo sapiens

<400> SEQUENCE: 7

Glu Val Thr Arg Ile Leu Asp Gly Lys
1               5

<210> SEQ ID NO 8
<211> LENGTH: 10
<212> TYPE: PRT
<213> ORGANISM: Homo sapiens

<400> SEQUENCE: 8

Arg Val Ala Pro Glu Glu His Pro Val Leu
1               5                   10

<210> SEQ ID NO 9
<211> LENGTH: 9
<212> TYPE: PRT
<213> ORGANISM: Homo sapiens

-continued

```
<400> SEQUENCE: 9

Glu Ala Gly Pro Ser Ile Val His Arg
1               5

<210> SEQ ID NO 10
<211> LENGTH: 9
<212> TYPE: PRT
<213> ORGANISM: Homo sapiens

<400> SEQUENCE: 10

Glu Ser Thr Gly Ser Ile Ala Lys Arg
1               5

<210> SEQ ID NO 11
<211> LENGTH: 11
<212> TYPE: PRT
<213> ORGANISM: Homo sapiens

<400> SEQUENCE: 11

Thr Ala Ala Asp Thr Ala Ala Gln Ile Thr Arg
1               5                   10

<210> SEQ ID NO 12
<211> LENGTH: 10
<212> TYPE: PRT
<213> ORGANISM: Homo sapiens

<400> SEQUENCE: 12

Asp Ala Ala His Pro Thr Asn Val Gln Arg
1               5                   10

<210> SEQ ID NO 13
<211> LENGTH: 9
<212> TYPE: PRT
<213> ORGANISM: Homo sapiens

<400> SEQUENCE: 13

Ala Glu Ser Leu Leu Thr Met Glu Tyr
1               5

<210> SEQ ID NO 14
<211> LENGTH: 10
<212> TYPE: PRT
<213> ORGANISM: Homo sapiens

<400> SEQUENCE: 14

Leu Leu Met Glu His Thr Met Val Ala Phe
1               5                   10

<210> SEQ ID NO 15
<211> LENGTH: 9
<212> TYPE: PRT
<213> ORGANISM: Homo sapiens

<400> SEQUENCE: 15

His Leu Ala Val Glu Arg Gly Lys Val
1               5

<210> SEQ ID NO 16
<211> LENGTH: 9
<212> TYPE: PRT
<213> ORGANISM: Homo sapiens

<400> SEQUENCE: 16
```

```
Ser Glu Ile Glu Ala Lys Val Arg Tyr
1               5

<210> SEQ ID NO 17
<211> LENGTH: 10
<212> TYPE: PRT
<213> ORGANISM: Homo sapiens

<400> SEQUENCE: 17

Thr Leu Phe Pro Gly Lys Val His Ser Leu
1               5                   10

<210> SEQ ID NO 18
<211> LENGTH: 9
<212> TYPE: PRT
<213> ORGANISM: Homo sapiens

<400> SEQUENCE: 18

Ser Glu Asp Asn Arg Ile Leu Leu Trp
1               5

<210> SEQ ID NO 19
<211> LENGTH: 9
<212> TYPE: PRT
<213> ORGANISM: Homo sapiens

<400> SEQUENCE: 19

Ser Ile Ile Gly Arg Leu Leu Glu Val
1               5

<210> SEQ ID NO 20
<211> LENGTH: 9
<212> TYPE: PRT
<213> ORGANISM: Homo sapiens

<400> SEQUENCE: 20

Gln Leu Val Asp Ile Ile Glu Lys Val
1               5

<210> SEQ ID NO 21
<211> LENGTH: 9
<212> TYPE: PRT
<213> ORGANISM: Homo sapiens

<400> SEQUENCE: 21

Ala Leu Leu Asp Lys Leu Tyr Ala Leu
1               5

<210> SEQ ID NO 22
<211> LENGTH: 9
<212> TYPE: PRT
<213> ORGANISM: Homo sapiens

<400> SEQUENCE: 22

Ile Met Leu Glu Ala Leu Glu Arg Val
1               5

<210> SEQ ID NO 23
<211> LENGTH: 9
<212> TYPE: PRT
<213> ORGANISM: Homo sapiens

<400> SEQUENCE: 23

Ala Glu Lys Leu Ile Thr Gln Thr Phe
1               5
```

<210> SEQ ID NO 24
<211> LENGTH: 9
<212> TYPE: PRT
<213> ORGANISM: Homo sapiens

<400> SEQUENCE: 24

Arg Leu Ala Gln His Ile Thr Tyr Val
1               5

<210> SEQ ID NO 25
<211> LENGTH: 9
<212> TYPE: PRT
<213> ORGANISM: Homo sapiens

<400> SEQUENCE: 25

Ser Glu Pro Asp Phe Val Ala Lys Phe
1               5

<210> SEQ ID NO 26
<211> LENGTH: 8
<212> TYPE: PRT
<213> ORGANISM: Homo sapiens

<400> SEQUENCE: 26

Thr Glu Val Thr Gly His Arg Trp
1               5

<210> SEQ ID NO 27
<211> LENGTH: 9
<212> TYPE: PRT
<213> ORGANISM: Homo sapiens

<400> SEQUENCE: 27

Ala Glu Thr Pro Asp Ile Lys Leu Phe
1               5

<210> SEQ ID NO 28
<211> LENGTH: 9
<212> TYPE: PRT
<213> ORGANISM: Homo sapiens

<400> SEQUENCE: 28

Gln Glu His Val Lys Ser Phe Ser Trp
1               5

<210> SEQ ID NO 29
<211> LENGTH: 9
<212> TYPE: PRT
<213> ORGANISM: Homo sapiens

<400> SEQUENCE: 29

Glu Glu Pro Thr Val Ile Lys Lys Tyr
1               5

<210> SEQ ID NO 30
<211> LENGTH: 9
<212> TYPE: PRT
<213> ORGANISM: Homo sapiens

<400> SEQUENCE: 30

Gln Glu Ala Gly Ile Lys Thr Ala Phe
1               5

```
<210> SEQ ID NO 31
<211> LENGTH: 9
<212> TYPE: PRT
<213> ORGANISM: Homo sapiens

<400> SEQUENCE: 31

Gly Glu Ala Ser Arg Leu Ala His Tyr
1               5

<210> SEQ ID NO 32
<211> LENGTH: 9
<212> TYPE: PRT
<213> ORGANISM: Homo sapiens

<400> SEQUENCE: 32

Gln Glu Asp Leu Arg Thr Phe Ser Trp
1               5

<210> SEQ ID NO 33
<211> LENGTH: 9
<212> TYPE: PRT
<213> ORGANISM: Homo sapiens

<400> SEQUENCE: 33

Met Glu Gln Val Ile Phe Lys Tyr Leu
1               5

<210> SEQ ID NO 34
<211> LENGTH: 9
<212> TYPE: PRT
<213> ORGANISM: Homo sapiens

<400> SEQUENCE: 34

Arg Leu Ala Ser Tyr Leu Asp Arg Val
1               5

<210> SEQ ID NO 35
<211> LENGTH: 9
<212> TYPE: PRT
<213> ORGANISM: Homo sapiens

<400> SEQUENCE: 35

Ile Glu His Gly Ile Ile Thr Asn Trp
1               5

<210> SEQ ID NO 36
<211> LENGTH: 9
<212> TYPE: PRT
<213> ORGANISM: Homo sapiens

<400> SEQUENCE: 36

Thr Thr Ala Glu Arg Glu Ile Val Arg
1               5

<210> SEQ ID NO 37
<211> LENGTH: 9
<212> TYPE: PRT
<213> ORGANISM: Homo sapiens

<400> SEQUENCE: 37

Glu Val Asn Gly Leu Ile Ser Met Tyr
1               5

<210> SEQ ID NO 38
<211> LENGTH: 9
```

-continued

```
<212> TYPE: PRT
<213> ORGANISM: Homo sapiens

<400> SEQUENCE: 38

Ala Glu Thr Ser Tyr Val Lys Val Leu
1               5

<210> SEQ ID NO 39
<211> LENGTH: 9
<212> TYPE: PRT
<213> ORGANISM: Homo sapiens

<400> SEQUENCE: 39

Lys Leu Ser Leu Gly Leu Pro Gly Leu
1               5

<210> SEQ ID NO 40
<211> LENGTH: 9
<212> TYPE: PRT
<213> ORGANISM: Homo sapiens

<400> SEQUENCE: 40

Ser Leu Gly Leu Gln Leu Ala Lys Val
1               5

<210> SEQ ID NO 41
<211> LENGTH: 9
<212> TYPE: PRT
<213> ORGANISM: Homo sapiens

<400> SEQUENCE: 41

Val Leu Asp Pro Arg Gly Ile Tyr Leu
1               5
```